United States Patent [19]

DiPippo

[11] Patent Number: 4,482,489

[45] Date of Patent: Nov. 13, 1984

[54] LIGHT-SENSITIVE DIAZONIUM TRIFLUOROMETHANE SULFONATES

[75] Inventor: Carmine A. DiPippo, Longmeadow, Mass.

[73] Assignee: James River Graphics, Inc., South Hadley, Mass.

[21] Appl. No.: 441,690

[22] Filed: Nov. 15, 1982

Related U.S. Application Data

[63] Continuation-in-part of Ser. No. 378,227, May 14, 1982, abandoned, which is a continuation of Ser. No. 208,072, Nov. 18, 1980, abandoned.

[30] Foreign Application Priority Data

| | | | |
|---|---|---|---|
| Nov. 16, 1981 | [DE] | Fed. Rep. of Germany | 3145406 |
| Nov. 16, 1981 | [FR] | France | 81 21367 |
| Nov. 16, 1981 | [NL] | Netherlands | 8105190 |
| Nov. 16, 1981 | [GB] | United Kingdom | 8134470 |

[51] Int. Cl.$^3$ .................. C07C 113/04; C07C 143/08; G03C 1/52; C07D 295/12

[52] U.S. Cl. ................................ 534/556; 260/513 R; 524/190; 204/159.11; 204/159.14; 430/136; 430/157; 430/163

[58] Field of Search ....... 260/141 R, 141 H, 141 AN, 260/141 S, 141 T, 142

[56] References Cited

U.S. PATENT DOCUMENTS

| | | | |
|---|---|---|---|
| 1,847,513 | 3/1932 | Hentrich et al. | 260/141 |
| 2,381,145 | 8/1945 | Von Glahn et al. | 260/141 X |
| 3,679,419 | 7/1972 | Gillich | 260/141 X |
| 4,039,521 | 8/1977 | Smith | 260/141 |
| 4,132,553 | 1/1978 | Burkle et al. | 260/141 X |

*Primary Examiner*—Floyd D. Higel

*Attorney, Agent, or Firm*—Burns, Doane, Swecker & Mathis

[57] ABSTRACT

Provided are light-sensitive diazonium compounds known as diazonium trifluoromethane sulfonates, which have the structural formula:

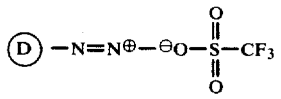

wherein Ⓓ—N=N— is the cation of a light-sensitive, aromatic diazonium compound. The diazonium trifluoromethane sulfonates are prepared as the reaction product of trifluoromethyl sulfonic acid, or a salt thereof, and a diazonium compound. Said diazonium trifluoromethane sulfonates find utility in diazography formulation for both positive- and negative-working diazotype photoreproduction systems, and as latent polymerization initiators activatable by irradiation.

5 Claims, No Drawings

LIGHT-SENSITIVE DIAZONIUM TRIFLUOROMETHANE SULFONATES

CROSS-REFERENCE TO RELATED APPLICATION

This application is a continuation-in-part of my eariler copending application Ser. No. 378,227, filed May 14, 1982, now abandoned, which is in turn a continuation of my earlier application Ser. No. 208,072, filed Nov. 18, 1980, now abandoned, both of which are hereby expressly incorporated by reference in their entireties and relied upon.

FIELD OF THE INVENTION

This invention relates to novel lightsensitive diazonium compounds, their preparation and uses thereof. More particularly, the present invention pertains to diazonium trifluoromethane sulfonates and formulations comprising same employable in diazotype materials. In another aspect of the present invention, said diazonium trifluoromethane sulfonates are useful as latent polymerization initiators for the photopolymerization of a polymerizable system.

DESCRIPTION OF THE PRIOR ART

Diazotype photoreproduction is, of course, a standard in the graphic arts. The touchstone of diazography process is the light-sensitivity of aromatic diazo salts and the fact that such salts undergo two different types of reactions: [1] replacement or decomposition, in which nitrogen is lost or evolves as nitrogen gas and some other atom or group attaches to the benzene ring in its stead; and [2] "coupling", wherein the nitrogen of the diazo function is retained and the salts react with certain couplable color-forming components, i.e., a "coupler" or "azo-coupling component", to effect formation of an azo dye species.

In positive-working diazo processes, a light-sensitive diazo-salt composition, which sensitizing formulation generally comprises a diazo compound, a coupling component or color former, and an acidic coupling inhibitor, is applied to a carrier or base, which may be paper or a transparent film such as cellulose acetate or a plastic coated base support, to form a positive-working material. The positive-working material is imaged by first exposing it through a master transparency or original. The light in the exposure step must supply sufficient energy to destroy the diazo compound in the areas corresponding to the clear background of the original.

The photochemical sensitivity of compounds typically employed in diazotype photographic reproduction materials resides in the near-ultraviolet region of the spectrum, and is centered about 400 nm (nanometers), one nm being equal to a millimicron or $10^{-9}$ meter; thus, medium-pressure, metal halide mercury lamps are generally used in performing this step. As a result, that part of the diazo coating which is unprotected from the ultraviolet radiation by the image of the original becomes a colorless substance, incapable of coupling with the "coupling" component, which is generally an aromatic amine, phenol, or aliphatic compound containing active methylene groups, to form colored oxyazo or aminoazo compounds known as azo dyes. The unaffected diazo compound which remains in those areas where the light has not struck, however, is able to form an azo dye by reaction with the coupling component when the medium is made alkaline to neutralize the acidic inhibitor. Thus, wherever there was an opaque line on the original, a dye-line appears on the copy. Positive-working, diazotype photoreproduction material is generally made alkaline, or pH adjusted, either by impregnating the material with ammonia vapors or passing it through an alkaline developing solution. See generally U.S. Pat. Nos. 1,444,469; 1,628,279; 2,217,189; 2,286,701; 2,429,249 and 2,694,009; German Patentschriften Nos. 56,606; 111,416; 487,247 and 515,205; British patent specification Nos. 234,818; 281,604 and 521,492.

In sensitizing formulations, the diazos are usually in the form of stabilized compounds of acidic salts such as zinc chloride, cadmium chloride, stannic chloride, and tetrafluoroborate salts, as well as hexafluorophosphate salts. These salts are used to stabilize the diazo and also to enhance the keeping quality or shelf life of sensitized diazotype material. Some selected diazos have also been prepared in the past as salts of perhalo-aliphatic carboxylic acids, e.g. trifluoroacetic acid (British patent specification No. 761,054); of aliphatic sulfonic acids such as methanesulfonic acid, and aromatic sulfonic acids such as benzenesulfonic acid, p-chlorobenzenesulfonic acid and 2,5-dichlorobenzenesulfonic acid, in the case of certain polymeric light-sensitive diazos (U.S. Pat. No. 3,679,419); and of the same or related aliphatic and aromatic sulfonic acids, including methanesulfonic acid and chloroethanesulfonic acid, in the case of yet other polymeric diazos, having high molecular weight (U.S. Pat. No. 4,132,553). Also, U.S. Pat. No. 2,381,145 discloses mixtures, or dry blends, of double salts of diazos (e.g. the zinc chloride double salt of diazo-4-chlor-2-nitraniline) with sulfonic acids of the formula $R(CH_2)_nSO_3$ in which n is a whole number, R is H, halogen, $SO_3H$, COOH, OH or an alkyl group which may be substituted with halogen, hydroxy, sulfo or the like, or their salts, e.g. methane sulfonic acid or the sodium salt of beta-chlor-ethane sulfonic acid.

It is also the general practice to provide some means of inhibiting print discoloration and image fading in sensitizing formulations. To achieve this end, various additives are generally used in diazo formulations, such as thiourea, thiourea derivatives and other similarly-acting compounds.

Notwithstanding the use of various stabilizers and additives in diazotype formulations, stability or shelf-life characteristics of diazotype materials have not been entirely satisfactory, particularly in diazotype materials sensitized with formulations employing diazos noted for their high coupling activity and/or instability.

Moreover, in formulating a sensitizing formulation, the greater the solubility of the diazos in the solvent system, the less solvent is generally required to obtain the desired or predetermined amount of diazo in solution and the less likely it is that problems with phenomena such as "blushing" are encountered. As well, the greater the solubility of the diazo, the higher the possible loading thereof in the solvent system, which, of course, provides for a denser image. Thus, the greater the solubility of a light-sensitive diazo compound, the greater the practical and economical convenience in using same.

The characteristic photodecomposition of certain aromatic diazo salts has also resulted in such salts being applicable in the role of a latent polymerization initiator for polymerizable systems such as those described in U.S. Pat. Nos. 3,816,279; 3,816,280; 3,816,281; 3,817,845; 3,817,850; 3,835,003; 3,997,344; 4,054,451; 4,054,452; 4,054,732; 4,056,393; 4,076,536; 4,080,274; and 4,091,194. Of course, diazonium salts which can be successfully employed in diazotype photoreproduction systems and, additionally, as latent polymerization initiators, possess increased commercial value due to their multiple important utilities.

Accordingly, a principal object of this invention is to provide novel salts of diazo compounds which can be employed to provide improved light-sensitive diazo formulations.

Another object of this invention is to provide novel diazo salt compositions having improved stability, shelf-life and compatability with plastic materials which are used as supports in diazotype photoreproduction materials.

A further object is to provide a diazo salt employable in not only a positive-working diazography system, but also in a negative-working diazography system.

Still, a further object of this invention is to provide a novel diazonium compound of increased solubility in organic solvents.

Yet another object of the present invention is to provide a diazonium compound which is also a suitable latent polymerization initiator for the photopolymerization of certain polymerizable systems.

Another important object of this invention is to provide an economical method of preparing a variety of diazo salt compounds, and to make practical the commercial utilization of many diazos, which have heretofore been considered uneconomical or difficult to manufacture.

Still another object of this invention is to provide improved diazotype photoreproduction materials and processes employing same.

Other objects, features and advantages will become apparent to those skilled in the art upon a study of this disclosure and the appended claims.

SUMMARY OF THE INVENTION

The aforementioned objects of the present invention are realized by means of certain novel diazonium salts. Thus, in accordance with this invention, there are provided novel, light-sensitive diazo compounds, which compounds are diazonium trifluoromethane sulfonates, also referred to herein as diazonium triflates, i.e. the trifluoromethyl sulfonic acid salts of diazo compounds, and a method for preparing same.

In another embodiment of the invention there are provided diazography formulations comprising a diazonium triflate (a diazonium salt of trifluoromethyl sulfonic acid), a diazo coupling component, and an acidic coupling inhibitor, which diazography formulation is useful in providing diazotype light-sensitive materials comprising a sheet material sensitized with said formulation.

Another embodiment of the invention pertains to a diazography composition comprising a novel diazonium triflate compound and an enolic, preferably phenolic, blocked-coupler or precursor of an azo coupling component adapted to be converted in the presence of an acid to an active azo coupling component, which composition is applicable to diazotype material comprising a sheet material sensitized with said composition. Such diazotype material is useful in negative-working diazotype photoreproduction.

A further embodiment of the present invention includes the use of diazonium triflates as latent polymerization initiators in compositions comprising the triflate and cyclic ester, e.g. lactone; a monomeric or prepolymeric epoxide; a cyclic ether such as an oxetane; or mixtures thereof; for the subsequent polymerization of said composition to higher molecular weights upon exposure to irradiation.

DETAILED DESCRIPTION OF THE PREFERRED EMBODIMENTS

More particularly, the novel diazonium triflates of the present invention are the trifluoromethyl sulfonic acid salts of a diazo compound, which can be represented by the following general formula:

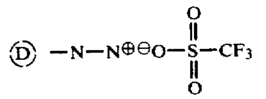

wherein Ⓓ—N=N— is the cation of an organic diazonium compound i.e. the cation of any diazonium compound, and in particular, known light-sensitive, aromatic diazonium compounds used in diazography formulations for diazotype photoreproduction, e.g. such as those diazonium compounds disclosed in U.S. Pat. Nos. 2,661,291; 2,694,010; 2,727,820; 2,861,065; 2,948,613; 3,082,200; 3,134,675; 3,164,468; 3,203,803; 3,255,011; 3,386,828; 3,407,066; and 3,816,280, especially such monomeric diazonium compounds. Accordingly, Ⓓ can be any unsubstituted or substituted mono or polycyclic aryl or heterocyclic aromatic, but is preferably selected from the group consisting of unsubstituted or substituted phenyl, naphthyl, anthryl, phenanthryl and azaheterocyclic aromatic moieties. Exemplary substituents thereof are those selected from the group consisting of, for example, an alkyl, alkylamino, dialkylamino, arylamino, aralkylamino, phenoxy, phenyl, phenyl thio ether, morpholino, piperidino, pyrrolidino, hexamethyleneimino, halide, alkoxy, cycloalkyl and piperazino radical. The type, position and number of substituents are without restriction, except of course, for generally applicable chemical principles. Most likely, same will be determined or chosen in accordance with the ultimate utility of the diazonium triflate. Para-substituted compounds, in general, have been found to be most useful and applicable to diazography utilities. Further, the preferred alkyl and alkoxy groupings are lower alkyl and alkoxy having from 1 to about 8 carbons; the preferred aryl groupings are of 6 to about 10 carbons; and, the preferred cycloalkyl groupings are of 3 to about 8 carbons. Illustrative of an azaheterocyclic aromatic moiety is a pyridyl radical, e.g. an aminopyridine derivative.

Typically, Ⓓ aryl or heteroaryl (e.g. phenyl, naphthyl, pyridyl, carbazole), which may be unsubstituted or substituted by one or more (generally, 1 to 3) groups which may be the same or different and which are preferably selected from the group consisting of halo (especially bromo or chloro); nitro; $C_1$-$C_7$ alkyl, optionally substituted by one or more $C_6$-$C_{10}$ aryl or halo; $C_3$-$C_8$ cycloalkyl; $C_6$-$C_{10}$ aryl, optionally substituted by one or more $C_1$-$C_7$ alkoxy, $C_1$-$C_7$ alkyl or $C_6$-$C_{10}$ aryl; $—NR_1R_2$ wherein $R_1$ and $R_2$, which can be the same or different, are each selected from the group consisting of $C_1$-$C_7$ alkyl (optionally substituted, e.g. by hydroxy or $C_6$-$C_{10}$ aryl), $C_3$-$C_8$ cycloalkyl, $C_6$-$C_{10}$ aryl (optionally substituted by $C_1$-$C_7$ alkyl or dialkylamino wherein each alkyl group contains 1 to 7 carbon atoms) and pyridyl (2, 3 or 4), or wherein one of $R_1$ and $R_2$ is defined as above and the other is hydrogen, or wherein $R_1$ and $R_2$ are combined such that $—NR_1R_2$ is a saturated cyclic amino radical optionally containing other hetero atoms such as N, S and O in the ring, e.g. morpholino, piperidino, pyrrolidino, hexamethyleneimino, piperazino, azabicyclononyl or oxazolidinyl, or any of the foregoing substituted by one or more $C_1$-$C_7$ alkyl, benzoyl or $C_1$-$C_7$ hydroxy alkyl groups; —X—R wherein X is oxygen or sulfur and R is $C_1$-$C_7$ alkyl, or $C_6$-$C_{10}$ aryl optionally by one or more $C_1$-$C_7$ alkyl or halo; —NHCO—$R_3$ wherein $R_3$ is $C_6$-$C_{10}$ aryl, $C_1$-$C_7$ alkyl or $C_1$-$C_7$ alkyl —S—$C_6$—$C_{10}$ aryl; —$NHSO_2$—$R_4$ wherein $R_4$ is $C_1$-$C_7$ alkyl; —$NHCOOR_5$ wherein $R_5$ is $C_1$-$C_7$ alkyl; and

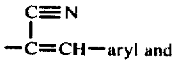 and 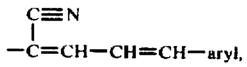

wherein the aryl group in each case contains 6 to 10 carbon atoms and can be unsubstituted or substituted (especially in the para position) by $C_1$-$C_7$ alkyl, halo, —X—R wherein X and R are defined as above, or $—NR_1R_2$ wherein $R_1$, $R_2$ and $—NR_1R_2$ are defined as above.

In a preferred embodiment of the invention, (D) is a substituted phenyl radical having one or more substituents, preferably 1 to 3 substituents, said substituents being selected from the group consisting of $C_1$-$C_7$ alkoxy, p-tolylthio, phenylthio, morpholino, $C_1$-$C_7$ alkyl-substituted morpholino, halo, pyrrolidino, $C_1$-$C_7$ alkyl, hexamethyleneimino, benzoylpiperidino, piperidino and benzamido. In a particularly preferred embodiment, (D) is para-substituted phenyl wherein the para-substituent is p-tolylthio, phenylthio, morpholino, $C_1$-$C_7$ alkyl-substituted morpholino, pyrrolidino, hexamethyleneimino (azacycloheptyl), benzoylpiperidino, piperidino or benzamido.

The diazonium triflates are prepared as the reaction product of trifluoromethyl sulfonic acid, or a salt thereof, and a diazonium compound.

The trifluoromethyl sulfonic acid, or salt thereof, used to prepare the diazo salt of the present invention may be in the form of the acid or any of its salts, and is most preferably in a form which is more soluble in the reaction medium than the diazo trifluoromethane sulfonate (diazo triflate) being prepared. The trifluoromethyl sulfonic acid reactant can be represented by $MOSO_2CF_3$, wherein M represents hydrogen, metallic or other cation, as for example, alkali metal such as K or Na, or ammonium salts.

The diazonium compounds which may be used in accordance with the present invention to react with the triflate can be represented by the general formula: (D)—N≡NX, wherein (D)—N≡N— is the same as before and X represents an anion capable of producing a stable diazonium compound. Basically, any diazonium compound, and in particular, known diazonium compounds used in diazography formulations for diazotype photoreproduction, can be employed, e.g. such as those diazonium compounds disclosed in the aforelisted U.S. Patents. Exemplary diazonium compounds include those formed from the following lists of exemplary cations ((D)—N≡N⊕) and anions (X⊖), which lists are not meant to be limitative.

CATIONS:

(1) p-chlorobenzenediazonium;
(2) 2,4-dichlorobenzenediazonium;
(3) 2,5-dichlorobenzenediazonium;
(4) 2,4,6-trichlorobenzenediazonium;
(5) p-methoxybenzenediazonium;
(6) o-methoxybenzenediazonium;
(7) 2-chloro-4- dimethylamino -5-methoxybenzenediazonium;
(8) 4-chloro-2,5-dimethoxybenzenediazonium;
(9) 2,4',5,-triethoxy-4-biphenyldiazonium [2,5-diethoxy-4-(p-ethoxyphenyl)benzenediazonium];
(10) 2,5-dimethoxy-4'-methyl-4-biphenyldiazonium [2,5-dimethoxy-4-(p-tolyl)benzenediazonium];
(11) 2,5-diethoxy-4-(phenylthio)benzenediazonium;
(12) 2,5-diethoxy-4-(p-tolylthio)benzenediazonium;
(13) p-morpholinobenzenediazonium;
(14) 2,5-dichloro-4-morpholinobenzenediazonium;
(15) 2,5-dimethoxy-4-morpholinobenzenediazonium;
(16) 4-(dimethylamino)naphthalenediazonium;
(17) 4-N,N-dimethylaminobenzenediazonium;
(18) 4-N,N-diethylaminobenzenediazonium;
(19) 4-N-ethyl-N-hydroxyethylaminobenzenediazonium;
(20) 4-N-methyl-N-hydroxyethylaminobenzenediazonium;
(21) 4-N-ethylaminobenzenediazonium;
(22) 4-N,N-diethylamino-2-methylbenzenediazonium;
(23) 4-N-ethyl-N-benzylaminobenzenediazonium;
(24) 4-N,N-diethylamino-3-chlorobenzenediazonium;
(25) 4-N-morpholino-2,5-diethoxybenzenediazonium;
(26) 4-(p-tolylthio)-2,5-diethoxybenzenediazonium;
(27) 4-(p-chlorophenoxy)-2,5-diethoxybenzenediazonium;
(28) 4-(p-ethoxyphenyl)-2,5-diethoxybenzenediazonium;
(29) 4-N,N-bis(μ-hydroxyethyl)aminobenzenediazonium;
(30) 4-N-pyrrolidino-3-methylbenzenediazonium;
(31) 4-N(2,6-dimethylmorpholino)benzenediazonium;
(32) 4-N-piperidinobenzenediazonium;
(33) 4-N-pyrrolidinobenzenediazonium;
(34) 4-N-hexamethyleneiminobenzenediazonium;
(35) 4-N-piperazinobenzenediazonium;
(36) 4-N-(N'-methylpiperazino)benzenediazonium;
(37) 4-N-{N-(3-azabicyclo[3.2.2]nonane}benzenediazonium;
(38) 4-N-[N'-(μ-hydroxyethyl)piperazino]benzenediazonium;
(39) 4-N-(N'-acetylpiperazino)benzenediazonium;
(40) 4-N-morpholino-2,5-diisopropoxybenzenediazonium;
(41) 4-N-azacycloheptane-2,5-diethoxybenzenediazonium;
(42) 6-dimethylamino-3-pyridinediazonium;
(43) 6-diethylamino-3-pyridinediazonium;
(44) 6-methylamino-3-pyridinediazonium;
(45) 6-ethylamino-3-pyridinediazonium;
(46) 6-morpholino-3-pyridinediazonium;
(47) 6-piperazino-3-pyridinediazonium;
(48) 6-benzylamino-3-pyridinediazonium;
(49) 6-p-toluidino-3-pyridinediazonium;
(50) 6-(p-dimethylaminoanilino)-3-pyridinediazonium;
(51) N,N'-(4,4'-biphenylene)bis(6-amino-3-pyridinediazonium);
(52) 6-anilino-3-pyridinediazonium;

(53) 6-(2-pyridylamino)-3-pyridinediazonium;
(54) 6,6'-(p,p'-methylenedianilino)bis(3-pyridinediazonium);
(55) N-methyl-6-anilino-3-pyridinediazonium;
(56) 6-dimethylamino-5-methyl-3-pyridinediazonium;
(57) 2-dimethylamino-3-pyridinediazonium;
(58) 4-N,N-diethylamino-2-ethoxybenzenediazonium;
(59) 4-N-ethylamino-2-methylbenzenediazonium;
(60) 4-N,N-dihydroxyethylaminobenzenediazonium;
(61) 4-N-oxazolidinobenzenediazonium;
(62) 4-N-methyloxazolidinobenzenediazonium;
(63) 4-N-(tetrahydro-1,3-oxazino)benzenediazonium;
(64) p-ethoxybenzenediazonium;
(65) 3-chloro-4,6-dimethoxybenzenediazonium;
(66) p-acetamidobenzenediazonium;
(67) 4-bromo-2,5-diethoxybenzenediazonium;
(68) 4-N-benzylamino-2-methoxy-5-methylbenzenediazonium;
(69) 4-N-benzoylamino-2-methoxy-5-methylbenzenediazonium;
(70) 4-N-phenylthioacetylamino-2,5-diethoxybenzenediazonium;
(71) 4'-acetylamino-2,5-diethoxy-4-biphenyldiazonium;
(72) 4-N-piperidino-5-methoxy-2-(p-tolylthio)benzenediazonium;
(73) 4-(p-tolylthio)-5-methoxy-2-piperidinobenzenediazonium;
(74) 4-N-morpholino-5-methoxy-2-(p-tolylthio)benzenediazonium;
(75) 4-N-piperidino-5-methoxy-2-piperidinobenzenediazonium;
(76) 4-N-piperidino-5-butoxy-2-(p-tolylthio)benzenediazoium;
(77) 4-N-piperidino-5-methoxy-2-phenoxybenzenediazonium;
(78) o-nitrobenzenediazonium;
(79) p-nitrobenzenediazonium;
(80) 4-nitro-2-methylebenzenediazonium;
(81) 4-methyl-2-nitrobenzenediazonium;
(82) 2,4-dimethyl-6-nitrobenzenediazonium;
(83) 3-chloro-4-pyrrolidinobenzenediazonium.
(84) 4-morpholino-3-methoxybenzenediazonium;
(85) 4-N-benzoylpiperidino-2,5-diisopropoxybenzenediazonium;
(86) 4-[(1-cyano-2-phenyl)vinyl]benzenediazonium;
(87) 4-[(1-cyano-2-p-chlorophenyl)vinyl]benzenediazonium;
(88) 4-[(1-cyano-2-p-methoxyphenyl)vinyl]benzenediazonium;
(89) 4-[(1-cyano-4-phenyl)buta-1,3-dien-1-yl]-benzenediazonium.

The preferred aromatic diazonium cations are those which, upon combination with the trifluoromethylsulfonate anion, $\ominus OSO_2CF_3$, readily form a precipitate, i.e. a reaction product which is insoluble in the reaction medium, which is generally water. Examples of diazonium cations which do form largely water insoluble triflates are the 4-(p-tolylthio)-2,5-diethoxybenzenediazonium; 4-N-morpholino-2,5-diisopropoxybenzenediazonium; and, 4-N-azacycloheptane-2,5-diethoxybenzenediazonium cations. Of course, the preference of any aromatic diazonium cation will ultimately depend upon the utility to which the diazonium triflate is destined. Indeed, if the diazonium triflate need exhibit some water solubility, then cations such as 4-N-ethyl-N-hydroxyethylaminobenzenediazonium and 4-N,N-diethylamino-2-methylbenzenediazonium would be more appropriate than the three aforenoted cations.

Among the specific cations listed above, those numbered (11), (12), (15), (24), (25), (30), (34), (40), (74), (77), (84) and (85) are presently preferred.

Anions:
(1) tetrafluoroborate,$BF_4^-$;
(2) hexafluorophosphate,$PF_6^-$;
(3) hexafluoroarsenate(V),$AsF_6^-$;
(4) hexafluroantimonate(V),$SbF_6^-$;
(5) pentachlorobismuthate(III),$BiCl_5^{-2}$;
(6) trichlorostannite,$SnCl_3^-$;
(7) trichlorozincate,$ZnCl_3^-$;
(8) chloride, $Cl^-$;
(9) sulfate, $SO_4^{-2}$;
(10) tetrachlorozincate, $ZnCl_4^{-2}$;
(11) hexachlorostannate (IV),$SnCl_6^{-2}$;
(12) tetrachloroferrate (III), $FeCl_4^-$;
(13) cadmium chloride, $CdCl_4^{-2}$;
(14) bisulfate, $HSO_4^-$.

The preferred anions are those which are capable of producing a stable diazo salt which is water soluble, e.g. diazos stabilized as salts of zinc chloride, cadmium chloride, stannic chloride, and boron trifluoride have been found to have appropriate water solubility. Accordingly, the hexachlorostannate, tetrachlorozincate and trichlorozincate, trichlorostannite, hexachlorostannite, tetrafluoroborate, as well as the chloride, bisulfate and sulfate anions, are among the most preferred anions. The water solubility imparted by the anions allow for greater facility in solubilizing the diazo compound in an aqueous reaction medium, and thus for a more practical preparation of the diazonium triflate via precipitation therefrom. The double salts of the cations can also be formed, and are appropriate for reaction with trifluoromethane sulfonic acid, or a salt thereof, to yield a diazonium triflate in accordance with the present invention.

The preparation of the diazonium triflates of the present invention can be illustrated by the following equation:

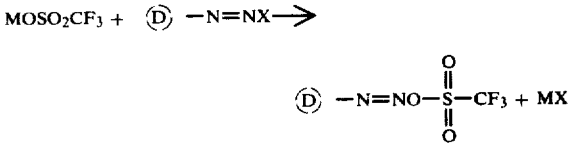

The reaction is generally carried out in an aqueous reaction medium to thereby allow recovery of the diazonium triflate product by precipitation from solution. Although the solubility of different diazo triflates will vary, some being less soluble in water than others, appropriate steps can be taken, for example, the conditions of temperature, volume, etc. can be accordingly adjusted, or seeding can be employed, in order to obtain a precipitate in virtually all cases. Due to the appreciable solubility of diazonium triflates in organic solvents, however, reaction in an organic solvent, such as hexane or a ketone, would not be practical if one intended to recover the diazonium triflate by precipitation from solution. If an organic reaction medium is employed, however, the triflate could still be recovered therefrom by using conventional extraction techniques, e.g. evaporation of the organic solvent.

The reaction in an aqueous medium is carried out by dissolving the diazo salt, (D)—N=NX, in the aqueous reaction medium. The trifluoromethyl sulfonic acid or salt, $MOSO_2CF_3$, is then introduced into the solution. Agitation of the solution can be employed to hasten the dissolution of the trifluoromethyl sulfonic acid. The temperature at which the reaction medium is maintained can vary greatly, with the thermal sensitivity of the diazo employed being determinative of a suitable temperature. Generally, however, temperatures ranging from ambient or room temperature to 75° C. can be employed, with temperatures in the range of about 25° C. to about 45° C. being preferred. Temperatures outside of these ranges, however, can also be employed. The amount of $MOSO_2CF_3$ added is preferably slightly in excess of the stoichiometric amount required for reaction with the diazo salt, which is a 1:1 molar ratio.

The aromatic diazonium cation Ⓓ—N═N⊕—and the trifluoromethyl sulfonate anion $^{\ominus}OSO_2CF_3$ always combine in a 1:1 molar ratio, and thus the exact composition of the reaction product Ⓓ—N═$NOSO_2CF_3$ is precisely predictable and does not from reaction to reaction. This stoichiometry also permits more exacting control of the formulations used in sensitizing diazotype materials.

Precipitation of the product diazonium triflate generally occurs without further treatment of the solution. However, in certain instances, precipitation may need to be initiated via adjustment in conditions, e.g., cooling of the aqueous reaction solution, or via seeding the solution. Upon precipitation of the product from solution, the diazonium triflate can be readily recovered via conventional techniques such as filtration.

In situ formation of the diazonium triflate is also possible. For example, in formulating a sensitizing composition, the composition can be formulated originally with a suitable diazo salt in place of the diazonium triflate. Subsequently, trifluoromethyl sulfonic acid can be added to produce the diazonium triflate in situ. Such technique can also be employed in the formation of a diazotype lightsensitive material, as the original solution or suspension applied to the base or support can be that comprising a suitable diazo salt capable of forming a diazonium triflate upon reaction with trifluoromethyl sulfonic acid. Accordingly, trifluoromethyl sulfonic acid is added to the treated base or support to form the diazonium triflate in situ.

In accordance with this invention, the following are examples of a number of specific diazonium triflates, same being obtainable by reacting a diazonium salt comprising the cation of said triflate and trifluoromethyl sulfonic acid or a salt thereof:

(1) p-N,N-diethylaminobenzenediazonium trifluoromethylsulfonate;
(2) 3-chloro-4-N,N-diethylaminobenzenediazonium trifluoromethylsulfonate;
(3) o-chlorobenzenediazonium trifluoromethylsulfonate;
(4) 4-N,N-diethylamino-2-ethoxybenzenediazonium trifluoromethylsulfonate;
(5) 4-N,N-diethylamino-2-methylbenzenediazonium trifluoromethylsulfonate;
(6) p-N,N-dimethylaminobenzenediazonium trifluoromethylsulfonate;
(7) 2,5-diisopropoxy-4-morpholinobenzenediazonium trifluoromethylsulfonate;
(8) 4-(3,5-dimethylmorpholino)benzenediazonium trifluoromethylsulfonate;
(9) o-methoxybenzenediazonium trifluoromethylsulfonate;
(10) 3-chloro-4-N-pyrrolidinobenzenediazonium trifluoromethylsulfonate;
(11) 3-methyl-4-N-pyrrolidinobenzediazonium trifluoromethylsulfonate;
(12) 3-methoxy-4-N-pyrrolidinobenzenediazonium trifluoromethylsulfonate;
(13) 5-methoxy-2-N-pyrrolidinobenzenediazonium trifluoromethylsulfonate;
(14) 2,4-dimethoxybenzenediazonium trifluoromethylsulfonate;
(15) 2,5-diethoxy-4-(4′-chlorophenoxy)benzenediazonium trifluoromethylsulfonate;
(16) 4-benzyloxybenzenediazonium trifluoromethylsulfonate;
(17) 2,5-diethoxy-4-N-benzamidobenzenediazonium trifluoromethylsulfonate;
(18) 2-methoxy-5-methyl-4-N-benzamidobenzenediazonium trifluoromethylsulfonate;
(19) p-ethoxybenzenediazonium trifluoromethylsulfonate;
(20) 4-chloronaphthalenediazonium trifluoromethylsulfonate;
(21) 4-pyrrolidinonaphthalenediazonium trifluoromethylsulfonate;
(22) p-chlorobenzenediazonium trifluoromethylsulfonate;
(23) 6-morpholino-3-pyridinediazonium trifluoromethylsulfonate;
(24) 6-dimethylamino-3-pyridinediazonium trifluoromethylsulfonate;
(25) 4-N-methanesulfonamido-2,5-dimethoxybenzenediazonium trifluoromethylsulfonate;
(26) 4-N-(2,6-dimethylmorpholino)benzenediazonium trifluoromethylsulfonate;
(27) 4-N,N-dimethylamino-3-chlorobenzenediazonium trifluoromethylsulfonate;
(28) 4-(p-tolylthio)-2,5-dimethoxybenzenediazonium trifluoromethylsulfonate;
(29) 4-N,N-diethylamino-3-methylbenzenediazonium trifluoromethylsulfonate;
(30) 4-(N-methyl-N-cyclohexyl)amino-3-chlorobenzenediazonium trifluoromethylsulfonate;
(31) 4-N,N-dimethylamino-3-pyridinediazonium trifluoromethylsulfonate;
(32) 2,5-diethoxy-4-(phenylthio)benzenediazonium trifluoromethylsulfonate;
(33) 2,5-dimethoxy-4-morpholinobenzenediazonium trifluoromethylsulfonate;
(34) 4-N-morpholino-2,5-diethoxybenezenediazonium trifluoromethylsulfonate;
(35) 4-N-hexamethyleneiminobenzenediazonium trifluoromethylsulfonate;
(36) 4-N-morpholino-5-methoxy-2-(p-tolylthio)benzenediazonium trifluoromethylsulfonate;
(37) 4-N-piperidino-5-methoxy-2-phenoxybenzenediazonium trifluoromethylsulfonate;
(38) 4-N-morpholino-3-methoxybenzenediazonium trifluoromethylsulfonate; and
(39) 4-N-benzoylpiperidino-2,5-diisopropoxybenzenediazonium trifluoromethylsulfonate.

Other examples of diazonium triflates include those of the structural formulae:

| Chemical Structure | Chemical Name |
|---|---|
| 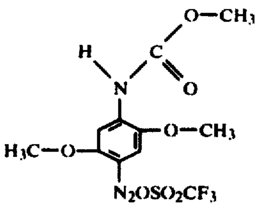 | 4-N—methoxycarbonylamino-2,5-dimethoxybenzenediazonium trifluoromethylsulfonate |
| 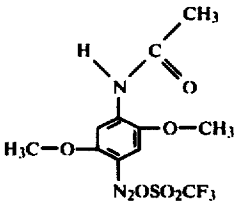 | 4-N—acetylamino-2,5-dimethoxybenzenediazonium trifluoromethylsulfonate |
| 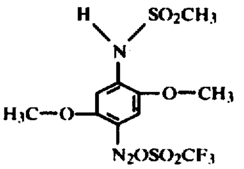 | 4-N—methylsulfonylamino-2,5-dimethoxybenzenediazonium trifluoromethylsulfonate |
| 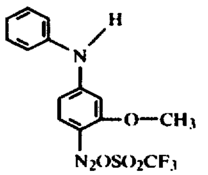 | 4-N—phenylamino-2-methoxybenzenediazonium trifluoromethylsilfonate |
| 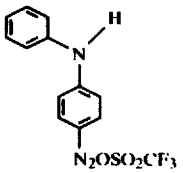 | 4-N—phenylaminobenzenediazonium trifluoromethylsulfonate |
| 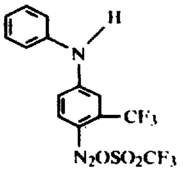 | 4-N—phenylamino-2-trifluoromethylbenzenediazonium trifluoromethylsulfonate |
| 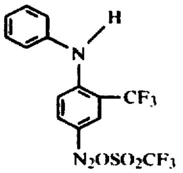 | 4-N—phenylamino-3-trifluoromethylbenzenediazonium trifluoromethylsulfonate |
| 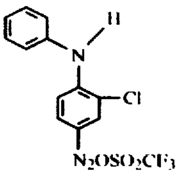 | 4-N—phenylamino-3-chlorobenzenediazonium trifluoromethylsulfonate |

-continued

| Chemical Structure | Chemical Name |
|---|---|
| 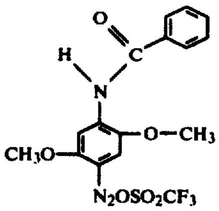 | 4-N—benzoylamino-2,5-dimethoxybenzenediazonium trifluoromethylsulfonate |
| 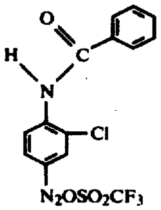 | 4-N—benzoylamino-3-chlorobenzenediazonium trifluoromethylsulfonate |
| 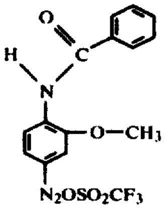 | 4-N—benzoylamino-3-methoxybenzenediazonium trifluoromethylsulfonate |
| 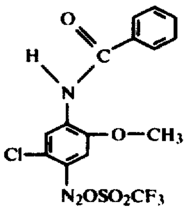 | 4-N—benzoylamino-2-chloro-5-methoxybenzenediazonium trifluoromethylsulfonate |
| 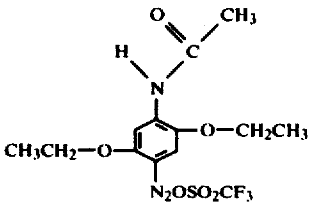 | 4-N—acetylamino-2,5-diethoxybenzenediazonium trifluoromethylsulfonate |
| 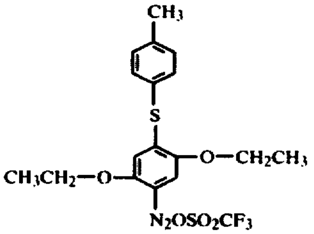 | 4-(p-tolylthio)-2,5-diethoxybenzenediazonium trifluoromethylsulfonate |
| 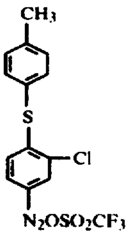 | 4-(p-tolylthio)-3-chlorobenzenediazonium trifluoromethylsulfonate |

-continued

| Chemical Structure | Chemical Name |
|---|---|
| 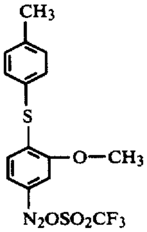 | 4-(p-tolylthio)-3-methoxybenzene-diazonium trifluoro-methylsulfonate |
| 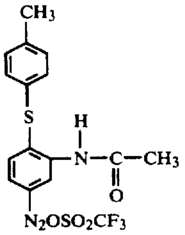 | 4-(p-tolythio)-3-N—acetylaminobenzene-diazonium trifluoro-methylsulfonate |
| 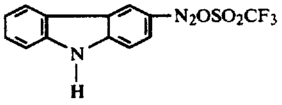 | carbazole-2-diazonium trifluoromethyl-sulfonate |
| 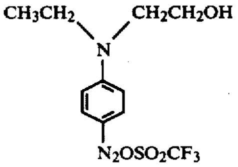 | 4-N—ethyl-N—hydroxyethylaminoben zenediazonium trifluoro-methylsulfonate |
| 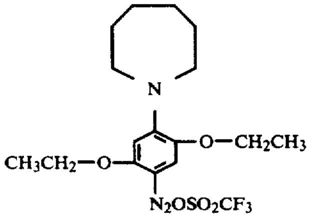 | 4-N—azacycloheptane-2,5-diethoxybenzene-diazonium trifluoro-methylsulfonate |
| 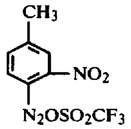 | 4-methyl-2-nitro-benzenediazonium tri-fluoromethylsulfonate |
| 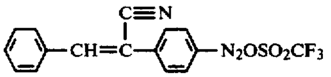 | 4-[(1-cyano-2-phenyl)-vinyl]benzenediazonium trifluoromethylsulfonate |
| 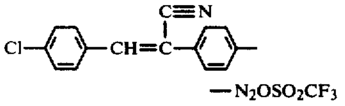 | 4-[(1-cyano-2-p-chloro-phenyl)vinyl]benzenedi-azoniumtrifluoromethyl-sulfonate |
| 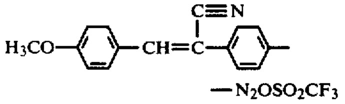 | 4-[(1-cyano-2-p-methoxy-phenyl)vinyl]benzenedi-azoniumtrifluoromethyl-sulfonate |
| 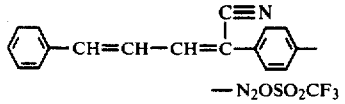 | 4-[(1-cyano-4-phenyl)-buta-1,3-dien-1-yl]ben-zenediazoniumtrifluoro-methylsulfonate |

-continued

| Chemical Structure | Chemical Name |
|---|---|
| 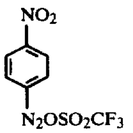 | p-nitrobenzene-diazonium trifluoro-methylsulfonate |

Of the specific diazonium triflates named above, the following species are among those presently preferred:

2,5-diisopropoxy-4-morpholinobenzenediazonium trifluoromethylsulfonate;
3 -chloro-4-N-pyrrolidinobenzenediazonium trifluoromethylsulfonate
3-methyl-4-N-pyrrolidinobenzenediazonium trifluoromethylsulfonate;
3-methoxy-4-N-pyrrolidinobenzenediazonium trifluoromethylsulfonate;
2,4-dimethoxybenzenediazonium trifluoromethylsulfonate;
2,5-diethoxy-4-N-benzamidobenzenediazonium trifluoromethylsulfonate;
4-(2,6-dimethylmorpholino)benzenediazonium trifluoromethylsulfonate;
4-(p-tolylthio)-2,5-dimethoxybenzenediazonium trifluoromethylsulfonate;
4-(p-tolylthio)-2,5-diethoxybenzenediazonium trifluoromethylsulfonate;
4-(p-tolylthio)-3-methoxybenzenediazonium trifluoromethylsulfonate;
4-N-azacycloheptyl-2,5-diethoxybenzenediazonium trifluoromethylsulfonate;
2,5-diethoxy-4-(phenylthio)benzenediazonium trifluoromethylsulfonate;
2,5-dimethoxy-4-N-morpholinobenzenediazonium trifluoromethylsulfonate;
4-N-morpholino-2,5-diethoxybenzenediazonium trifluoromethylsulfonate;
4-N-hexamethyleneiminobenzenediazonium trifluoromethylsulfonate;
4-N-morpholino-5-methoxy-2-(p-tolylthio)benzenediazonium trifluoromethylsulfonate;
4-N-piperidino-5-methoxy-2-phenoxybenzenediazonium trifluoromethylsulfonate;
4-N-morpholino-3-methoxybenzenediazonium trifluoromethylsulfonate; and
4-N-benzoylpiperidino-2,5-diisopropoxybenzenediazonium trifluoromethylsulfonate.

The diazonium triflates of the present invention are light-sensitive and undergo the same chemical reactions that characterize aromatic diazo salts. Accordingly, diazonium triflates are useful in diazography processes. There are also definite advantages, however, to using diazonium triflates in diazography processes, namely, the $^{\ominus}OSO_2CF_3$ anion, in general, imparts a property of lower water solubility to aromatic diazonium cations with which it is combined as compared to such conventional diazo stabilized salts of zinc chloride, cadmium chloride, stannic chloride, and the like. This lower water solubility facilitates the economical manufacture of stabilized diazonium triflates in aqueous media.

Moreover, it has also been found that diazonium triflates exhibit a property of greatly increased organic solvent solubility as compared to conventional diazo salts, including diazonium hexafluorophosphates. This increased solubility in organic solvents such as ketones, alcohols, and the like, which are used for applying diazo formulations to plastic layers or carriers in making diazotype materials, aids in the loading of a solvent with the diazo formulation; and, in providing a diazotype material with improved resistance to "blushing". The condition known as "blushing" is a result of poor compatibility of a diazosalt with the plastic layer or carrier of a diazotype material, thereby producing a haze on the plastic layer which impairs its transparency and general appearance. The increased solubility of diazonium triflates in the solvent used for applying same to carriers helps to minimize blushing and also provide for denser images Another important advantage of using diazonium triflates, in comparison to known inorganic fluoride diazo salts such as tetrafluoroborates and hexafluorophosphates, is that triflates do not liberate a corrosive gas, e.g., hydrogen fluoride, during decomposition upon exposure to light as the aforenoted salts. Such gas is very corrosive to glass and can thereby cause rapid deterioration of light sources, which can result in reduced image quality.

Sensitizing compositions comprising diazonium triflates which are useful in diazographic applications can be easily formulated. Diazonium triflates are most adaptable to positive-working diazotype photoreproduction systems by formulating a sensitizing composition comprising a diazonium triflate as the light sensitive diazonium compound, a diazo coupling component, and an acidic coupling inhibitor as is known in the diazography art, e.g., as disclosed in U.S. Pat. Nos. 3,203,803; 2,694,010; 3,255,011; and 2,948,613. The coupling component can be any conventional diazo coupler which is normally employed in diazotype materials. Illustrative thereof are: 2,3-dihydroxynaphthalene; 1,8-dihydroxynaphthalene; phloroglucinol; resorcinol; octylresorcinol; alpharesorcylamid; 3-methyl-1-phenyl-5-pyrazalone; acetoacetanilide; N-benzylacetoacetamide; 2,3-dihydroxynaphthalene-6-sulfonic acid; 2,5-xylenol; 6,7-dihydroxy-2-naphthalenesulfonic acid; 2,3-naphthalenediol; m-hydroxyphenylurea; 4,4'-thiodiresorcinol; 3,5-dihydroxybenzoic acid; $\beta$-oxynaphthoic acid monoethanol amide; and mixtures thereof. The acid coupling inhibitor can also be any conventional and well known inhibitor generally employed in diazotype materials, e.g., citric acid, tartaric acid, boric acid, and the like.

In addition to the foregoing materials there can also be included reagents commonly employed in diazotype photoreproduction materials, as for example, intensifiers such as ammonium sulfate, zinc chloride or nickel sulfates; stabilizing agents such as thiourea, or thiosinamine; accelerators such as 1-allyl-3-betahydroxyethylthiourea or 1-allylthiourea; hygroscopic agents such as gylcol or glycerin; and wetting agents such as saponin, lauryl sulfate, aryl benzene sulfonate or oleyl-N-methyltaurine.

Moreover, there can be included finely divided or colloidal silica or alumina, and/or aqueous dispersions or colloidal solutions of organic film-forming binders, such as colloidal water-soluble polyvinyl alcohol, hydroxyethylcellulose, methyl cellulose, gelatine or the like, or latex-like dispersions of polyvinyl acetate, polyvinyl chloride, polyvinyl chloride-acetate, polyvinylidene chloride, polyacrylonitrile or polymethylmethacrylate.

In order to form a positive-working diazotype light-sensitive material, the components of the aforedescribed sensitizing formulation are preferably incorporated into a single solution or suspension, and applied in a single coating step to a base or support. The base may be paper, or a film such as regenerated cellulose, cellulose acetate butyrate, cellulose acetate propionate, silica/-polyvinylbutyral or other plastic films, but most preferably it is a base comprising a polyethylene terephthalate (polyester) film. Other conventional substrates such as textile substrates and nonwovens may also be used. See generally the U.S. Pat. No. 3,976,491 to Desjarlais.

Upon application of the diazonium triflate comprising sensitizing formulation, a diazotype light-sensitive material comprising a substrate sensitized with said formulation is obtained. Said sensitized material can then be subjected to light, i.e., ultraviolet light, to decompose the diazo in the unmasked area, and then same can be developed to allow the undecomposed diazo and coupler to react to form a diazo dye..

The diazonium triflates of the present invention are also employable in the Bennett negative-working diazotype photoreproduction system, as disclosed in U.S. Pat. No. 4,252,884. The senitizing formulation for such a system comprises a diazonium triflate in the dual role of diazonium compound and light-sensitive acid progenitor, and at least one acid labile enolic, preferably phenolic, blocked coupler adapted to be converted in the presence of acid to an active azo-coupling component. Preferably, the blocked-coupler has a structural formula selected from the group consisting of

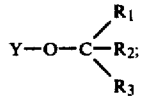

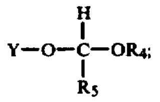

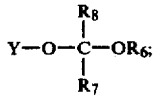

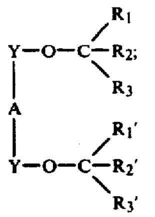

$Y—O—CH_2—O—CH_2CH_2—OCH_3$; and

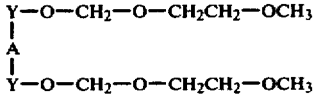

wherein $R_1$, $R_2$, $R_3$, $R_4$, $R_5$, $R_6$, $R_7$, $R_8$, $R_1'$, $R_2'$ and $R_3'$ which may be the same or different, are selected from the group consisting of alkyl, preferably straight or branched chain lower alkyl of from 1 to 8 carbons; alkenyl, preferably lower alkenyl of from 2 to about 8 carbons; alkynyl, preferably lower alkynyl of from 2 to about 8 carbon atoms; aryl, preferably aryl having from 6 to about 10 carbons; cycloalkyl, preferably cycloalkyl constituting from 3 to about 8 carbons; aralkyl, alkaryl, aralkenyl and alkenylaryl, preferably wherein the alkyl, aryl and alkenyl groups are as above defined; and, where $R_5$ may also be hydrogen; wherein Y is aryl, e.g., phenyl, naphthyl, anthryl, phenanthryl, and the like; and A is any suitable bridging linkage, e.g., an alkylene group or a direct chemical bond. Moreover, any two or three of said R substituents may be linked together to form a cyclic, bicyclic or heterocyclic structure.

Illustrative of suitable acid labile phenolic blocked-couplers for the Bennett negative-working system are the following: 1-naphthyl triphenylmethyl ether; 1-methylcyclopentyl 1-naphthyl ether; 1-butoxy-1-(1-naphthoxy)ethane; t-butyl phenyl ether; 2-(1-naphthoxy)3-methylbutane; 1-(1-butoxy)-1-(1-naphthoxy)ethane; 1,2-bis(5-t-butoxy-1-naphthyl)ethane; dibenzo(d,f)-2,2-dimethyl-1,3-dioxepine; dibenzo(d,f)-2-methyl-2-phenyl-1,3-dioxepine; dibenzo(d,f)-2,2-diphenyl-1,3-dioxepine; 2,2′-di(2-tetrahydropyranoxy)diphenyl; 2,3-isopropylidenedioxynaphthalene, t-butyl 1-naphthyl ether; 1-naphthyl 2-tetrahydropyranyl ether; benzo(e)-2-phenyl-1,3-dioxin; 1-t-butoxy-5-benzylnaphthalene; t-butyl (4-bromo-1-naphthyl) ether; dibenzo(d,f)-2-methyl-1,3-dioxepine; β-methoxyethoxymethyl α-naphthyl ether; and 3-(methoxyethoxymethoxy)-N-(2-ethylphenyl)-2-naphthalamide.

The enolic-blocked coupler can be used with any effective diazonium triflate. Examples of the most preferred, however, include those diazonium triflates previously listed. It should be appreciated, however, that while the coupler and diazonium salt molecules may bear any one or more substituents which will not interfere with the acid catalyzed unblocking chemistry, at least two sites must be available on the blocked-coupler for any rearrangement and for the subsequent coupling of the unblocked molecule to form an azo dye.

A negative-working diazotype photoreproduction material according to the invention can be conveniently produced by first preparing a solution in pure organic solvents of the two essential components, i.e., a solution of the diazonium triflate and blocked-coupler. The preferred solvents are generally low molecular weight ketones and alcohols because same, e.g., are typically good solvents for the diazonium triflates. Diazonium triflates, however, are extremely soluble in any organic solvent and therefore the choice need not be limited to ketones and alcohols. In practice, however, it has generally been found advantageous to utilize a mixture of ketone and alcohol solvents.

The blocked-coupler is generally dissolved in the solvent solution with moderate mechanical stirring, then the diazonium triflate is added and dissolved in a similar manner, although the components may be added in reverse order. Conventional additives, such as intensifiers, accelerators, hydroscopic agents or wetting agents, can also be added to the composition.

One preferred additive is benzotriazole, the incorporation of which into negative-working diazography formulations has been found to improve both the contrast and line acuity of the images derived therefrom when incorporated in an effective amount for same. The amount of benzotriazole has generally been found to be effective when the molar ratio of benzotriazole to diazonium salt in the formulation is in the range from about 1:20 to 1:100.

While the amounts of the respective components formulated are not especially critical, it has been determined for the Bennett negative-working system that incorporation of the diazonium triflate in amounts of up to 7 parts by weight per 100 g of total mix is eminently practicable, preferably not less than 0.5 parts by weight of total mix. The blocked-coupler is typically incorporated in a ratio of 0.1 mole per mole diazonium triflate to 2.0 moles per mole diazonium triflate. Preferably, the composition contains a quantity of approximately 1.0 mole of blocked-coupler per approximately 1.0 mole of diazonium triflate.

Conveniently, the immediately aforesaid diazonium triflate composition or formulation is applied to any suitable base substrate, e.g., cellulose acetate butyrate, cellulose acetate propionate, ethylcellulose, silica/-polyvinylbutyral, and preferably to coatings of the aforementioned materials borne by a transparent or opaque polyethylene terephthalate (polyester) film base, by imbibition or bead coating. It is preferred that approximately 30 grams of mix are laid down per square yard. This consumption varies according to the specific components utilized, the type and thickness of the polymer, precoating, and the image density desired. Preferably, the subbed base is overcoated with a layer of cellulose ester, ether, or the like; or the coating can itself comprise a like matrix resin in addition to the solution of the imaging chemicals. A representative film prepared according to the invention would comprise a 0.92–7 mil bond coated polyester base, overcoated with, e.g., a 0.25 mil matrix resin (for example, cellulose acetate propionate) overcoating including the imaging chemicals. Other suitable substrates include the conventional diazo paper bases, textile substrates, nonwovens, etc. See generally the U.S. Pat. No. 3,976,491 to Desjarlais.

While the imaging components may all be coated in a single layer, the components may also be in separate layers. For example, the diazonium triflate may be coated onto a matrix coated polyester, a barrier layer applied, then a second matrix layer may be applied to this and the blocked-coupler imbibed into such second layer.

The resulting light-sensitive diazotype material comprising a support member coated with the diazonium triflate formulation can then be imaged by exposing same to light of a quality and quantity sufficient to photochemically liberate catalytic amounts of acid from the diazonium triflate upon decomposition thereof. Reaction of the liberated acid with the blocked-couplers results in an unblocking thereof to yield active azo-couplers. Development of the diazotype material under alkaline conditions produces coupling of the active azo-coupler with undecomposed diazonium triflate in the light-struck areas to form an azo dye. The diazotype material can be heated prior to or during development to a temperature between about 100° and 210° F.

The background areas of the developed film are then preferably cleared in a neutral environment by exposing the same to overall actinic light for a period of about 60 seconds to decompose all the unreacted salt. While this final step is not required, it is generally preferable to include it.

In a further embodiment of the present invention, the diazonium triflates can be employed as latent polymerization initiators in the polymerization of epoxides, cyclic ethers such as oxetanes, cyclic esters such as lactones, and/or mixtures thereof, as discussed in more detail hereinbelow. The process involves forming a mixture of a material polymerizable to higher molecular weights comprising a lactone monomer, an oxetane, a monomeric or prepolymeric epoxide, or mixtures thereof, and a radiation sensitive aromatic diazonium salt which decomposes upon application of energy thereto to liberate a product which thereby initiates the polymerization of said material. Such polymerization processes are described in U.S. Pat. Nos. 3,816,279; 3,816,280; 3,816,281; 2,817,845; 3,817,850; 3,835,003; 3,997,344; 4,054,451; 4,054,452; 4,054,732; 4,056,393; 4,076,536; 4,080,274; and 4,091,194. See, also "The Photoinitiated Cationic Polymerization of Epoxy Resins", J. V. Crivello et al, *Epoxy Resin Chemistry*, ACS Symposium Series 114, ed. Ronald S. Bauer, Chapter 1, pp. 1-16; and "Photosensitized Epoxides as a Basis for Light-Curable Coatings", William R. Watt, *Epoxy Resin Chemistry*, ACS Symposium Series 114, ed. Ronald S. Bauer, Chapter 2, pp. 17-45.

Similarly, diazonium triflates decompose upon irradiation thereof to liberate a product which, when in the presence of cyclic ether or ester monomers such as oxetanes, epoxides or lactones, provides cleavage of the carbon-oxygen bond of said ether or ester to thereby initiate growth of a polymeric chain or formation of a cross-linkage. One theoretical mechanism, it being emphasized that same is only theoretical and that applicant does not wish to be bound thereby, is that upon decomposition a triflate aryl ester is formed which then extracts a proton, e.g., from the reaction medium, to form an acid. Said acid is the active agent which then cleaves the carbon-oxygen bond to initiate the polymerization or cross-linkage, and also the agent which reacts with the blocked-coupler of the aforedescribed negative-working diazography system. Thus, as are the photosensitive aromatic diazonium salts mentioned in the aforenoted patents, diazonium triflates are applicable as latent polymerization initiators.

Numerous epoxides can be utilized in the polymerization initiation aspects of the present invention, including many commercially available epoxy resins, which can be liquid or solid, solid resins being generally preferred when the polymerization system is intended for use in an imaging system which may be stored for some time prior to carrying out polymerization reaction. In particular, suitable epoxides include epichlorohydrin/bisphenol A epoxy resins (which contain varying amounts of the diglycidyl ether of bisphenol A), for example, those available under the trade designations Epon 828, Epon 1004, Epon 1009F. and Epon 1010 from Shell Chemical Co. and those designated DER-331, DER-332 and DER-334 from Dow Chemical Co.; vinylcyclohexane dioxide, for example ERL-4206 from Union Carbide Corp.; 3,4-epoxycyclohexylmethyl-3,4-epoxycyclohexane carboxylate, e.g. ERL-4221 from Union Carbide Corp.; 3,4-epoxy-6-methylcyclohexylmethyl-3,4-epoxy-6-methylcyclohexane carboxylate, e.g. ERL-4201 from Union Carbide Corp.; bis(3,4-epoxy-6-methylcyclohexylmethyl)adipate, e.g. ERL-4289 from Union Carbide Corp.; bis(2,3-epoxycyclopentyl) ether, e.g. ERL-0400 from Union Carbide Corp.; aliphatic epoxy modified with propylene glycol, e.g. ERL-4050 and ERL-4052 from Union Carbide Corp.; dipentene dioxide, e.g. ERL-4269 from Union Carbide Corp.; epoxidized polybutadiene, e.g. Oxiron 2001 from FMC Corp.; silicon resin containing epoxy functionality; flame retardant epoxy resins, e.g. DER-580, a brominated bisphenol type epoxy resin available from Dow Chemical Co.; 1,4-butadiene diglycidyl ether of phenol-formaldehyde Novolak, e.g. DEN-431 and DEN-4 from Dow Chemical Co.; and resorcinol diglycidyl ether, for example Heloxy WC-69 from Wilmington Chemical, Inc. Some of these and other possible epoxides for use herein are disclosed by William H. Watt, "Photosensitized Epoxides as a Basis for Light-Curable Coatings", ACS Symposium Series 114, ed. Ronald S. Bauer, Chapter 2, pp. 17-45, who worked with vinyl cyclohexane dioxide; allyl glycidyl ether; butanediol diglycidyl ether; 3,4-epoxycyclohexylmethyl-3,4-epoxycyclohexane carboxylate; DGEBA (with a viscosity at 25° C. of 4000-6000 cps); epoxy phenol novolak (with a viscosity at 25° C. of 1400-2000 cps); bis(3,4-epoxy-6-methylcyclohexylmethyl)adipate; $C_{12}$-$C_{14}$ alkyl glycidyl ether; and other epoxides.

Moreover, polymeric hydroxy-containing resins can be used in combination with epoxy compounds for use in the present invention. Such polymeric materials can be copolymerized with epoxy resins by the action of the instant diazonium triflates. Representative polymeric hydroxy-containing materials include polyoxyethylene and polyoxypropylene glycols and triols of molecular weights from about 200 to about 10,000 corresponding to equivalent weights of 100 to 5,000 for the diols and 70 to 3,300 for the triols; polytetramethylene glycols of varying molecular weight; copolymers of hydroxypropyl and hydroxyethyl acrylates and methacrylates with other free radical-polymerizable monomers such as acrylate esters, vinyl halides or styrene; copolymers containing pendant hydroxyl groups; modified cellulose polymers such as hydroxyethylated and hydroxypropylated cellulose; hydroxy-terminated polyesters and hydroxy-terminated polylactones and hydroxy-terminated polyalkadienes. Useful commercially available hydroxy-containing materials include the Polymeg® series of polytetramethylene ether glycols such a Polymeg® 650, 1000 and 2000, available from Quaker Oats Co.; the PeP series of polyoxyalkylene tetrols having secondary hydroxyl groups such as PeP 450, 550 and 650, available from Wyandotte Chemicals Corp.; the Butvar series of polyvinylacetal resins such as Butvar B-72A, B-73, B-76, B-90 and B-98 and Formvar 7/70, 12/85, 7/95S, 7/95E, 15/95 S and 15/95 E, available from Montsanto Chemical Co.; the PCP series of polycaprolactone polyols such as PCP 0200, 0210, 0230, 0240 and 0300, available from Union Carbide Corp.; Paraplex U-148, an aliphatic polyester diol available from Rohm & Haas; the Multron R series of saturated polyester polyols such as Multron R-2, R-12A, R-16, R-18, R-38, R-68 and R-74, available from Mobay Chemical Co.; Klucel E, a hydroxypropylated cellulose having an equivalent weight of approximately 100 available from Hercules, Inc.; and Alcohol Soluble Butyrate, a cellulose acetate butyrate ester having a hydroxyl equivalent weight of approximately 400, available from Eastman Kodak.

Yet other epoxy resins for use in photoinsolubilization according to the present invention are described in copending Bennett et al U.S. Ser. No. 403,108 filed July 29, 1982, incorporated by reference herein in its entirety and relied upon.

Preferred diazonium triflates for use in the photoinsolubilization aspects of this invention generally are those in which (D) is substituted aryl, preferably para-substituted. Most preferably (D) is a radical of the formula

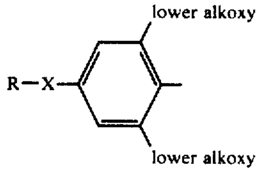

in which —X—R is defined as hereinabove. In a most preferred embodiment X—R is phenylthio or p-tolylthio. Generally speaking, the instant compounds wherein the aryl substituent is $—NR_1R_2$ are far less preferred for use as photopolymerization initiators than are the other triflates disclosed herein.

Representative compounds useful for photoinsolubilization of resins in accord with the present invention include the following:

(1) p-chlorobenzenediazonium trifluoromethylsulfonate;
(2) 2,4-dichlorobenzenediazonium trifluoromethylsulfonate;
(3) 2,5-dichlorobenzenediazonium trifluoromethylsulfonate;
(4) 2,4,6-trichlorobenzenediazonium trifluoromethylsulfonate;
(5) 2,4,6-tribromobenzenediazonium trifluoromethylsulfonate;
(6) o-nitrobenzenediazonium trifluoromethylsulfonate;
(7) p-nitrobenzenediazonium trifluoromethylsulfonate;
(8) 2-methyl-4-nitrobenzenediazonium trifluoromethylsulfonate;
(9) 4-methyl-2-nitrobenzenediazonium trifluoromethylsulfonate;
(10) 2,4-dimethyl-6-nitrobenzenediazonium trifluoromethylsulfonate;
(11) 4-chloro-2,5-dimethoxybenzenediazonium trifluoromethylsulfonate;
(12) 2,5-diethoxy-4-(p-ethoxyphenyl)benzenediazonium trifluoromethylsulfonate;
(13) 2,5-dimethoxy-4-p-tolylbenzenediazonium trifluoromethylsulfonate;
(14) 2,5-diethoxy-4-(phenylthio)benzenediazonium trifluoromethylsulfonate;
(15) 2,5-diethoxy-4-(p-tolylthio)benzenediazonium trifluoromethylsulfonate;
(16) 4-[(1-cyano-2-p-methoxyphenyl)vinyl]benzenediazonium trifluoromethylsulfonate;
(17) 4-[(1-cyano-2-phenyl)vinyl]benzenediazonium trifluoromethylsulfonate;
(18) 4-[(1-cyano-2-p-chlorophenyl)vinyl]-benzenediazonium trifluoromethylsulfonate; and
(19) 4-[(1-cyano-4-phenyl)buta-1,3-dien-1-yl]-benzenediazonium trifluoromethylsulfonate.

A general application of the process for employing diazonium triflates as latent polymerization initiators involves admixing a diazonium triflate, with or without the use of a suitable solvent, with a polymerizable monomer or mixture of monomers, or with other polymerizable material (e.g., a mixture of epoxy resin and polymeric hydroxy-containing resin). By a suitable inert solvent is meant one that does not react appreciably with the polymerizable material or the aryldiazonium compound before exposure to actinic radiation. Examples of such solvents include the dimethyl ether of diethylene glycol, anisole, acetonitrile, butyronitrile, toluene, acetone, xylene, methyl ethyl ketone, ethyl ether, cellosolve ether, 1,1,2,2-tetrachloroethane, monochlorobenzene, o-chlorotoluene, o-dichlorobenzene, trichloroethylene, propylene carbonate, and the like. Mixtures of these solvents may be employed, particularly if mixtures of epoxides are employed. It is to be understood, however, that the use of solvents is not mandatory.

The amount of photosensitive compound employed in the admixture need not be specifically ascertained but is related to the amount of monomer being polymerized. Quite satisfactory results can be obtained by providing a diazonium triflate in catalytic amounts, preferably an amount by weight of from about 0.5 to about 5% of the catalyst precursor relative to the weight of the polymerizable material provided, about 2% or less being amply effective with some of the monomer-catalyst precursor systems.

The polymerizable mixture is thereafter coated on a suitable substrate, such as a metal plate, plastic or paper, and the substrate is exposed to ultraviolet or electron beam radiation. On exposure, the triflate decomposes and provides initiation of the polymerization of the monomer or monomers via cleavage of carbon-oxygen bonds.

The source of radiation for carrying out the method of the present invention can be any suitable source, such as the ultraviolet actinic radiation produced from a mercury, xenon, or carbon arc, or the light produced by a cathode ray tube. The only limitation placed on the radiation source used is that it must have an energy level at the irradiated film sufficient to impart to the polymerizable system energy at an intensity high enough to reach the decomposition level of the photosensitive compounds. The wavelength (frequency) range of actinic radiation is generally chosen to obtain sufficient absorption of energy to execute the desired decomposition.

Such polymerization systems can also be used in imaging systems. For example, a mixture of the monomers with epoxides, which may contain a suitable solvent in substantial proportions, is coated on a metal plate, dried if necessary to remove solvent present, and the plate is exposed to ultraviolet light through a mask or negative. The light initiates polymerization which propagates rapidly in the exposed image areas. The resulting polymer in the exposed areas is resistant to many or most solvents and chemicals, while the unexposed areas can be washed with suitable solvents to leave a reversal image of a polymer.

It may be desirable to include in the composition comprising the diazonium triflate and polymerizable material an inert pigment or filler, which may be present in even a major proportion by weight, or small amounts of inert nonvolatile liquids such as mineral oil. Inclusion of such inert ingredients usually makes advisable a proportionate increase in the optimum amount of catalyst precursor used. Nevertheless, the precursors needed rarely exceeds 5% of the entire weight of the composition.

It may further be desirable to include stabilizers or gelation inhibitors for said mixtures of monomers and catalyst. Suitable compounds for such purpose may be sulfoxides such as methyl sulfoxide, propyl sulfoxide, the 1-oxide of tetrahydrothiophene, and the like as disclosed in U.S. Pat. No. 3,711,391; organic amides and ureas such as N,N-dimethylacetamide and 1,1,3,3-tetramethylurea as disclosed in U.S. Pat. No. 3,711,390;

cyclic amides such as 1-methyl-2-pyrrolidinone, poly(1-vinyl-2-pyrrolidinone), and the like as disclosed in U.S. Pat. No. 3,721,617 and organic nitriles such as acetonitrile as disclosed in U.S. Patent No. 3,721,616. When employed as disclosed in said patents, the inhibitors are utilized in amounts which may vary from about 0.5 to 5% of the weight of the polymerizable material present in the composition, an amount of inhibitor of less than about 1% by weight of polymerizable material being nearly always sufficient.

In order to further illustrate the present invention, the following specific examples are given, it being understood that same are intended only as illustrative and nowise limitative.

EXAMPLE 1

This example illustrates the preparation of the diazonium triflate, 4-(p-tolylthio)-2,5-dimethoxybenzenediazonium trifluoromethylsulfonate. The representative equation for the reaction is as follows:

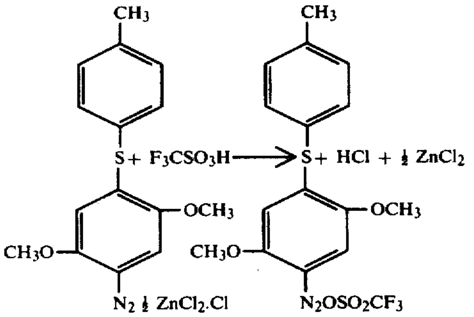

41.3 Grams of the 4-(p-tolylthio)-2,5-dimethoxybenzenediazonium zinc chloride double salt and 400 ml of water are placed in a 800 ml beaker. The resulting mixture is stirred and heated to 65° C. for 30 minutes to yield a hazy solution with suspended solids therein. The solution is clarified of insolubles and the filtrate cooled to about 50°-55° C.

15 Grams of trifluoromethylsulfonic acid are added dropwise, upon which a yellow copious precipitate forms. The slurry is cooled to about 10° C. and then filtered to recover the yellow precipitate. The recovered solids are then washed with a small amount of water, and dried via suction. 33.0 Grams of product are obtained.

To the above initial insolubles are added 400 ml of water. The solution is heated to 65° C., and then clarified of insolubles as before. 5.0 Grams of trifluoromethylsulfonic acid are added to the clarified solution resulting in the formation of a yellow precipitate. The yellow solids are recovered as above to obtain 7.2 grams of purified product, m.p. 106°-108° C.

EXAMPLE 2

30.5 Grams of 3-chloro-4-N-pyrrolidinobenzenediazonium zinc chloride salt are placed in a 500 ml beaker and water is added thereto, with stirring, until complete dissolution of the diazo salt occurs. The temperature of the resulting solution is about 35°-40° C., with a total of about 300 ml of water having been added. To the solution mixture, which is cloudy, are added two spatulas of filter aid and one spatula of Nuchar. The slurry is then clarified via filtration to yield a clear, bright orange solution The orange solution is cooled to about 20° C. and 1 grams of trifluoromethylsulfonic acid are added thereto at such a rate that a 20° C. temperature is maintained. From the first drop of acid, turbidity develops, with precipitation increasing throughout the course of addition. Upon completion of addition, the resulting slurry is stirred for 15 minutes at a temperature of about 10°-15° C., and then filtered to recover a yellow-green precipitate.

The yellow-green solids are washed with a minimal amount of water and dried via suction. The solids are also dried overnight over $P_2O_5$. 18.5 Grams of diazonium triflate product are recovered.

EXAMPLE 3

In Example 3, the preparation of various diazonium triflates via the following general extraction scheme is illustrated:

To a beaker equipped with magnetic stirring is added 1.0 mole of the respective diazo zinc salt. The mole of diazo zinc salt is added in a 1:1 (by volume) methylene chloride: water solution containing 13% of said salt. As the solution is stirred in the beaker, 1.05 moles of trifluoromethylsulfonic acid is added dropwise thereto from an addition funnel. The solution is allowed to stir for about five minutes. An amount of the salt equal to 80% of a saturated aqueous saline solution is then added to the beaker, and stirring is allowed to continue until the added salt dissolves (approximately 15 minutes). The contents of the beaker are emptied into a separatory funnel, and a split in layers is allowed to occur, with the organic layer being dropped into an Erlenmeyer flask. The organic layer is dried over sodium sulfate, and diluted to three times its volume with hexane. The resulting solution is stirred vigorously and chilled, and then suction filtered to recover diazonium triflate solid. The solid is protected from the light while it is washed with hexane and allowed to dry or filtered under vacuum.

In Run 1, a 3-methyl-4-(N,N-diethylamino)benzenediazonium zinc salt is reacted with trifluoromethylsulfonic acid in accordance with the aforedescribed procedure. 3-Methyl-4-(N,N-diethylamino)benzenediazonium triflate having a melting point of 90°-93° C. is recovered in a 52% yield.

In Run 2, a 2,5-diethoxy-4-(p-tolylthio)benzenediazonium zinc salt is reacted with trifluoromethylsulfonic acid to provide 2,5-diethoxy-4-(p-tolylthio)benzenediazonium triflate, having a melting point of 101° to 104° C., in an 85% yield.

In Run 3, a 3-methyl-4-N-pyrrolidinobenzenediazonium zinc salt is reacted in accordance with the aforedescribed scheme. 3-Methyl-4-N-pyrrolidinobenzenediazonium triflate, melting in the range of 119° to 122° C., is recovered in a 61% yield.

In Run 4, a 3-chloro-4-N-pyrrolidinobenzenediazonium zinc salt is reacted with trifluoromethylsulfonic acid in accordance with the aforedescribed process. 3-Chloro-4-N-pyrrolidinobenzenediazonium triflate, with a melting point range of 90° to 93° C., is recovered in a yield of 63%.

EXAMPLE 4

Example 4 illustrates the formulation of a positive working, light-sensitive diazotype system and the use thereof in making a light-sensitive diazotype material:

| | |
|---|---|
| A solution of | |
| 2,2'-Dihydroxybiphenyl | 1.18 grams |
| 4-(p-Tolylthio)-2,5-diethoxy-benzenediazonium trifluoromethyl-sulfonate | 1.84 grams |
| Methyl alcohol | 55 cc |
| Acetone | 40 cc |
| Methyl cellosolve | 5 cc |
| 5-Sulfosalicylic acid | .25 gram |
| Zinc chloride | .5 gram |
| Eastman CAP 482.20 | 12.35 grams |

is prepared to yield a clear lacquer with a viscosity of approximately 800 centipoise. The lacquer is applied with a suitable coating device to a 4 mil prebonded polyester base support and dried 3.5 minutes at 75°-80° C.

The coated material is covered with a printed sheet and exposed to an ultraviolet light source of 400-420 nanometers. The exposed material is passed, without the master, through a standard diazo processor to yield an orange-yellow image reproduction of the master.

EXAMPLE 5

The procedure of Example 4 is followed except that 4-N-pyrrolidino-3-chlorobenzenediazonium trifluoromethylsulfonate is employed as the diazonium triflate. Upon exposure and processing of the light sensitive material, a sepia image reproduction of the master is obtained.

EXAMPLE 6

Example 6 illustrates the formulation of a negative-working, light-sensitive, diazotype system and the use thereof in making a light-sensitive diazotype material:

| | |
|---|---|
| A solution of | |
| 4-(p-Tolylthio)-2,5-dimethoxy-benzenediazonium trifluoromethylsulfonate | 4.30 grams |
| t-butyl naphthyl ether | 2.00 grams |
| Acetone | 50 cc |

is coated on a suitably pre-bonded polyester base using an appropriate coating unit and dried at 75°-80° C. for 3.5 minutes. The coating base is exposed through a printed sheet, heated 15 seconds on a SCOTT 24 preheater and developed by passing through a Model 6000 dry developer, subsequently cleared of unused diazo from the back for 60 seconds in a SCOTT 716 microcopier. There is obtained a red-purple image with transparent images corresponding to the image of the original master. That is, the image sign has been reversed.

EXAMPLE 7

Use of an appropriate 4-N-phenylamino-2-methoxybenzenediazonium zinc chloride salt in the general procedure of Example 1 or 2 above affords 4-N-phenylamino-2-methoxybenzenediazonium trifluromethylsulfonate, melting at 105°-107° C.

EXAMPLE 8

49 Grams of 4-N-morpholino-2,5-diisopropoxybenzenediazonium zinc chloride salt, 164 ml of methylene chloride and 164 ml of water are placed in a 600 ml beaker and 20.7 grams of trifluoromethane sulfonic acid are added dropwise. Within approximately 5 minutes, complete dissolution is obtained. 47 Grams of sodium chloride are then added and the reaction mixture is stirred for about 15 minutes. To the resultant solution, 20 ml of water are added. The mixture is then placed in a separatory funnel and separated. The organic layer is dried with sodium sulfate, then diluted with 600 ml of hexane, stirred and chilled for one hour. The crystals which form are washed with hexane. There are thus obtained 38 grams of 4-N-morpholino-2,5-diisopropoxybenzenediazonium trifluoromethylsulfonate, melting at 114°-119° C.

EXAMPLE 9

Example 9 illustrates the use of representative trifluoromethylsulfonates of the present invention as photopolymerization initiators.

The representative epoxy resin employed is Epon 1009 F, an epichlorohydrin/bisphenol A epoxy resin obtained from Shell Chemical Company. It can be represented by the structural formula

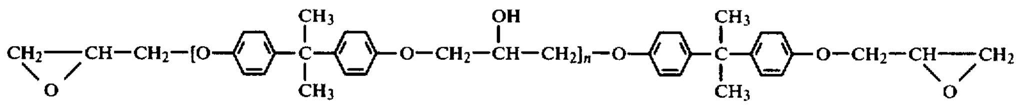

and is a solid with a melting point range of 145°-155° C. Its epoxide equivalent is 2300-3800, i.e. the grams of resin containing one gram-equilavent of epoxide, as determined by the perchloric acid method (ASTMD 1625); it has a viscosity of 100-250 centipoise (as determined at 25° C. using a 40% solution of resin in methyl ethyl ketone); and it has a Gardner Holdt viscosity of Z2-Z5 (ASTMD 1725-62).

1.5 Grams of 2,5-diethoxy-4-(p-tolylthio)-benzenediazonium trifluoromethanesulfonate are dissolved in a solution of 30 grams of Epon 1009 F in 70 grams of methyl CelloSolve, and the resultant solution is coated onto a subbed polyethylene terephthalate film, using a #16 Mayer coating rod. Both subbed and unsubbed sides are coated in individual variations. The film is then dried at 100° C. for 3 minutes. 3"×6" Strips of flim are exposed to a Berkey light source for 3 minutes, with approximately half of each strip being covered from exposure. The strips are returned to the 100° C. oven for 3 minutes and then washed with solvent (methyl CelloSolve or methyl ethyl ketone). The exposed portion of the film has the appearance of frosted glass, indicating successful photoinsolubilization.

EXAMPLE 10

1.5 Grams of 2,5-diethoxy-4-(p-tolylthio)benzenediazonium trifluoromethylsulfonate are dissolved in a solution of 30 grams of Epon 1009 F in 70 grams of methyl Cellosolve, and the resultant solution is coated onto a subbed polyethylene terephthalate film, using a #16 Mayer rod. The coating is placed on the subbed side of the film and is then dried at 245° F. for 3 minutes. 3"×6" Strips of film are exposed to a Berkey light source for 3 minutes, then returned to the 245° F. oven for 3 minutes and thereafter washed with methyl ethyl ketone or methyl Cellosolve. A very clear image is obtained, indicating excellent photoinsolubilization.

Substantial repetition of the foregoing procedure, utilizing 1.5 grams of 4-(p-tolylthio)-2,5-dimethoxybenzenediazonium trifluoromethylsulfonate in place of the 2,5-diethoxy-4-(p-tolylthio)benzenediazonium trifluoromethylsulfonate, likewise affords a very clear image. The image obtained is especially clear when 0.8 gram of Pylam Solvent Blue (a blue dye) is added to the formulation prior to coating.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What we claim is:

1. A monomeric diazonium trifluoromethane sulfonate having the structural formula:

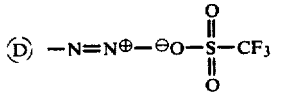

wherein (D) —N=N— is the cation of a light-sensitive, aromatic diazonium compound.

2. A compound as defined in claim 1 wherein (D) comprises a phenyl, naphthyl, anthryl, phenanthryl, or azaheterocyclic aromatic moiety.

3. A compound as defined in claim 2 wherein (D) is a substituted phenyl, naphthyl, anthryl, or phenanthryl moiety having one or more substituents, which may be the same or different, and which are alkyl, alkylamino, dialkylamino, arylamino, aralkylamino, phenoxy, phenyl, phenyl thio ether, morpholino, piperidino, pyrrolidino, hexamethyleneimino, halo, alkoxy, cycloalkyl or piperazino.

4. A compound as defined in claim 1 wherein (D) is $C_6$-$C_{10}$ aryl or heteroaryl, unsubstituted or substituted by one or more radicals, which may be the same or different, selected from the group consisting of halo; nitro; $C_1$-$C_7$ alkyl, unsubstituted or substituted by one or more halo or $C_6$-$C_{10}$ aryl; $C_3$-$C_8$ cycloalkyl; $C_6$-$C_{10}$ aryl, unsubstituted or substituted by one or more $C_1$-$C_7$ alkoxy, $C_1$-$C_7$ alkyl or $C_6$-$C_{10}$ aryl; —$NR_1R_2$ wherein $R_1$ and $R_2$, which may be the same or different, are each selected from the group consisting of $C_1$-$C_7$ alkyl unsubstituted or substituted by hydroxy or $C_6$-$C_{10}$ aryl, $C_3$-$C_8$ cycloalkyl, $C_6$-$C_{10}$ aryl unsubstituted or substituted by $C_1$-$C_7$ alkyl or dialkylamino wherein each alkyl group contains 1 to 7 carbon atoms, and pyridyl, or wherein one of $R_1$ and $R_2$ is defined as above and the other is hydrogen, or wherein $R_1$ and $R_2$ are combined such that —$NR_1R_2$ is morpholino, piperidino, pyrrolidino, hexamethyleneimino, piperazino, azabicyclononyl or oxazolidinyl, any of which cyclic radicals may be unsubstituted or substituted by one or more $C_1$-$C_7$ alkyl, benzoyl or $C_1$-$C_7$ hydroxyalkyl groups; —X—R wherein X is oxygen or sulfur and R is $C_1$-$C_7$ alkyl, or $C_6$-$C_{10}$ aryl unsubstituted or substituted by one or more $C_1$-$C_7$ alkyl or halo; —NHCO—$R_3$ wherein $R_3$ is $C_6$-$C_{10}$ aryl, $C_1$-$C_7$ alkyl or $C_1$-$C_7$ alkyl—S—$C_6$-$C_{10}$ aryl; —$NHSO_2$—$R_4$ wherein $R_4$ is $C_1$-$C_7$ alkyl; —NH-$COOR_5$ wherein $R_5$ is $C_1$-$C_7$ alkyl; and

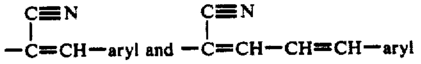

wherein the aryl group in each instance contains 6 to 10 carbon atoms and may be unsubstituted or substituted by one or more $C_1$-$C_7$ alkyl, halo, —X—R wherein X and R are defined as above or —$NR_1R_2$ wherein $R_1$, $R_2$ and —$NR_1R_2$ are as above.

5. The compound as defined in claim 1 which is:

p-N,N-diethylaminobenzenediazonium trifluoromethylsulfonate;

3-chloro-4-N,N-diethylaminobenzenediazonium trifluoromethylsulfonate;

o-chlorobenzenediazonium trifluoromethylsulfonate;

4-N,N-diethylamino-2-ethoxybenzenediazonium trifluoromethylsulfonate;

4-N,N-diethylamino-2-methylbenzenediazonium trifluoromethylsulfonate;

p-N;N-dimethylaminobenzenediazonium trifluoromethylsulfonate;

2,5-diisopropoxy-4-morpholinobenzenediazonium trifluoromethylsulfonate;

4-(2,6-dimethylmorpholino)benzenediazonium trifluoromethylsulfonate;

o-methoxybenzenediazonium trifluoromethylsulfonate;

3-chloro-4-N-pyrrolidinobenzenediazonium trifluoromethylsulfonate;

3-methyl-4-N-pyrrolidinobenzenediazonium trifluoromethylsulfonate;

3-methoxy-4-N-pyrrolidinobenzenediazonium trifluoromethylsulfonate;

5-methoxy-2-N-pyrrolidinobenzenediazonium trifluoromethylsulfonate;

2,4-dimethoxybenzenediazonium trifluoromethylsulfonate;

2,5-diethoxy-4-(4'-chlorophenoxy)benzenediazonium trifluoromethylsulfonate;

4-benzyloxybenzenediazonium trifluoromethylsulfonate;

2,5-diethoxy-4-N-benzamidobenzenediazonium trifluoromethylsulfonate;

2-methoxy-5-methyl-4-N-benzamidobenzenediazonium trifluoromethylsulfonate;

p-ethoxybenzenediazonium trifluoromethylsulfonate;

4-chloronaphthalenediazonium trifluoromethylsulfonate;

4-pyrrolidinonaphthalenediazonium trifluoromethylsulfonate;

p-chlorobenzenediazonium trifluoromethylsulfonate;

6-morpholino-3-pyridinediazonium trifluoromethylsulfonate;

6-dimethylamino-3-pyridinediazonium trifluoromethylsulfonate;

4-dimethylamino-3-pyridinediazonium trifluoromethylsulfonate;

4-N-methoxycarbonylamino-2,5-dimethoxybenzenediazonium trifluoromethylsulfonate;

4-N-acetylamino-2,5-dimethoxybenzenediazonium trifluoromethylsulfonate;

4-N-methylsulfonylamino-2,5-dimethoxybenzenediazonium trifluoromethylsulfonate;

4-N-phenylamino-2-methoxybenzenediazonium trifluoromethylsulfonate;

4-N-phenylaminobenzenediazonium trifluoromethylsulfonate;

4-N-phenylamino-2-trifluoromethylbenzenediazonium trifluoromethylsulfonate;
4-N-phenylamino-3-trifluoromethylbenzenediazonium trifluoromethylsulfonate;
4-N-phenylamino-3-chlorobenzenediazonium trifluoromethylsulfonate;
4-N-benzoylamino-2,5-dimethoxybenzenediazonium trifluoromethylsulfonate;
4-N-benzoylamino-3-chlorobenzenediazonium trifluoromethylsulfonate;
4-N-benzoylamino-3-methoxybenzenediazonium trifluoromethylsulfonate;
4-N-benzoylamino-2-chloro-5-methoxybenzenediazonium trifluoromethylsulfonate;
4-N-acetylamino-2,5-diethoxybenzenediazonium trifluoromethylsulfonate;
4-(p-tolylthio)-2,5-diethoxybenzenediazonium trifluoromethylsulfonate;
4-(p-tolylthio)-3-N-acetylaminobenzenediazonium trifluoromethylsulfonate;
carbazole-2-diazonium trifluoromethylsulfonate;
4-N-ethyl-N-hydroxyethylaminobenzenediazonium trifluoromethylsulfonate;
4-N-azacycloheptyl-2,5-diethoxybenzenediazonium trifluoromethylsulfonate;
4-methyl-2-nitrobenzenediazonium trifluoromethylsulfonate;
p-nitrobenzenediazonium trifluoromethylsulfonate;
4-N,N-dimethylamino-3-chlorobenzenediazonium trifluoromethylsulfonate;
4-(p-tolylthio)-2,5-dimethoxybenzenediazonium trifluoromethylsulfonate;
4-N,N-diethylamino-3-methylbenzenediazonium trifluoromethylsulfonate;
4-(3,5-dimethylmorpholino)benzenediazonium trifluoromethylsulfonate;
4-N-methanesulfonamido-2,5-dimethoxybenzenediazonium trifluoromethylsulfonate;
4-N-methyl-N-cyclohexylamino-3-chlorobenzenediazonium trifluoromethylsulfonate;
4-(p-tolylthio)-3-chlorobenzenediazonium trifluoromethylsulfonate;
4-(p-tolylthio)-3-methoxybenzenediazonium trifluoromethylsulfonate;
2,5-diethoxy-4-(phenylthio)benzenediazonium trifluoromethylsulfonate;
2,5-dimethoxy-4-morpholinobenzenediazonium trifluoromethylsulfonate;
4-N-morpholino-2,5-diethoxybenezenediazonium trifluoromethylsulfonate;
4-N-hexamethyleneiminobenzenediazonium trifluoromethylsulfonate;
4-N-morpholino-5-methoxy-2-(p-tolylthio)benzenediazonium trifluoromethylsulfonate;
4-N-piperidino-5-methoxy-2-phenoxybenzenediazonium trifluoromethylsulfonate;
4-N-morpholino-3-methoxybenzenediazonium trifluoromethylsulfonate;
4-N-benzoylpiperidino-2,5-diisopropoxybenzenediazonium trifluoromethylsulfonate;
4-[(1-cyano-2-phenyl)vinyl]benzenediazonium trifluoromethylsulfonate;
4-[(1-cyano-2-p-chlorophenyl)vinyl]benzenediazonium trifluoromethylsulfonate;
4-[(1-cyano-2-p-methoxyphenyl)vinyl]benzenediazonium trifluoromethylsulfonate; or
4-[(1-cyano-4-phenyl)buta-1,3-dien-1-yl]-benzenediazonium trifluoromethylsulfonate.

* * * * *